US00PP34102P2

(12) United States Plant Patent
Ruigrok

(10) Patent No.: US PP34,102 P2
(45) Date of Patent: Apr. 5, 2022

(54) ***DAHLIA* PLANT NAMED 'BKDAMAGFF'**

(50) Latin Name: *Dahlia hybrida*
Varietal Denomination: BKDAMAGFF

(71) Applicant: BEEKENKAMP PLANTS B.V., Maasdijk (NL)

(72) Inventor: Sanne Helena Ruigrok, Hillegom (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/346,277

(22) Filed: Jun. 13, 2021

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ... A01H 5/02; A01H 5/00; A01H 6/14; A01H 6/144
See application file for complete search history.

*Primary Examiner* — June Hwu
(74) *Attorney, Agent, or Firm* — C. Anne Whealy

(57) ABSTRACT

A new and distinct cultivar of *Dahlia* plant named 'BKDAMAGFF', characterized by its upright to somewhat outwardly spreading and sturdy plant habit; moderately vigorous growth habit; dense and bushy growth habit; dark green-colored leaves; freely flowering habit; large decorative type inflorescences with reddish orange and yellow bi-colored ray florets; and good garden performance.

2 Drawing Sheets

Figure 1:
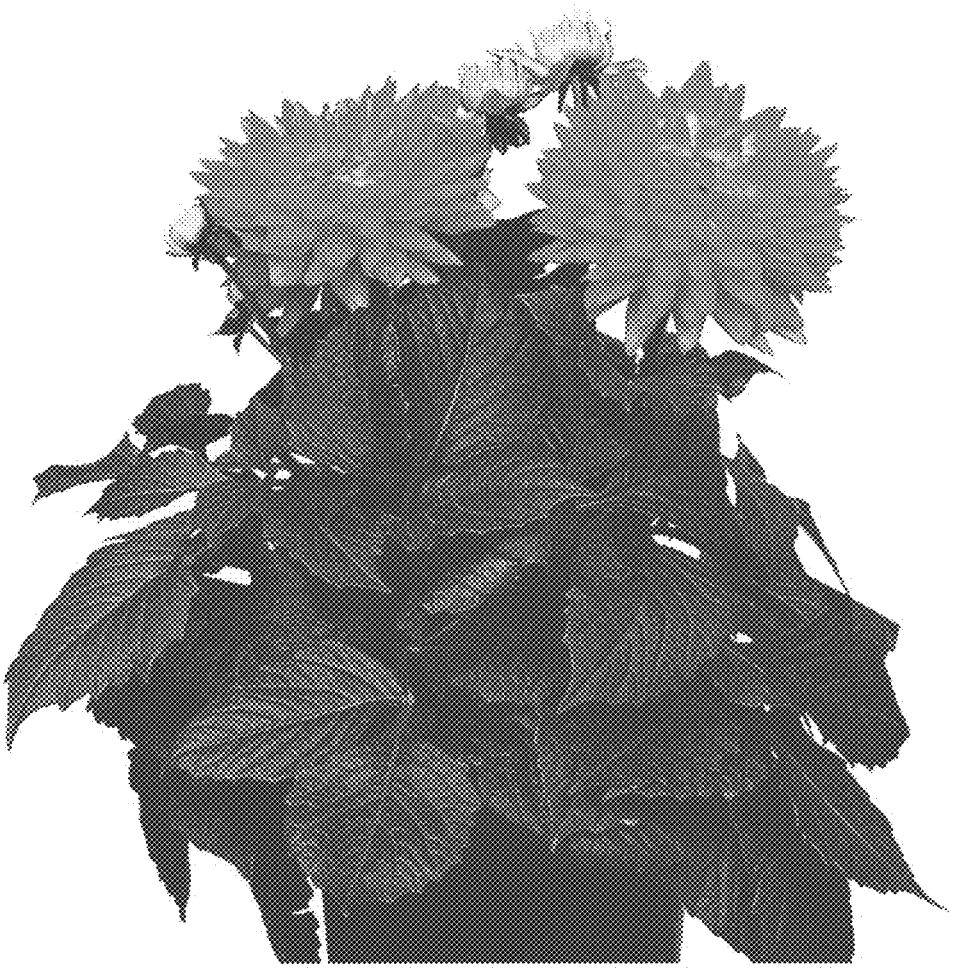

Botanical designation: *Dahlia hybrida.*
Cultivar denomination: 'BKDAMAGFF'.

STATEMENT REGARDING PRIOR DISCLOSURES BY INVENTOR/APPLICANT and ASSIGNEE

An European Community Plant Breeder's Rights application for the instant plant was filed by the Applicant/Assignee of the instant application, Beekenkamp Plants B.V. of Maasdijk, The Netherlands on Oct. 20, 2020, application number 2020/2576. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Dahlia* plant, botanically known as *Dahlia hybrida* and hereinafter referred to by the name 'BKDAMAGFF'.

The new *Dahlia* plant is a product of a planned breeding program conducted by the Inventor in Hillegom, The Netherlands. The objective of the breeding program is to create new vigorous container *Dahlia* plants with large inflorescences with attractive ray floret coloration.

The new *Dahlia* plant originated from a cross-pollination in September, 2016 in Hillegom, The Netherlands of a proprietary selection of *Dahlia hybrida* identified as code number FET.S15.001.002, as the female, or seed, parent with a proprietary selection of *Dahlia hybrida* identified as code number FET. S15.001.032, not patented, as the male, or pollen, parent. The new *Dahlia* plant was discovered and selected by the Inventor as a single flowering plant from within the progeny of the stated cross-pollination in a controlled greenhouse environment in Hillegom, The Netherlands in September, 2017.

Asexual reproduction of the new *Dahlia* plant by terminal cuttings in a controlled greenhouse environment in Hillegom, The Netherlands since March, 2018 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural conditions. The phenotype may vary somewhat with variations in environmental conditions such as temperature and light intensity, without, however, any variance in genotype.

The following traits have been repeatedly observed and are determined to be the unique characteristics of 'BKDAMAGFF'. These characteristics in combination distinguish 'BKDAMAGFF' as a new and distinct *Dahlia* plant:

1. Upright to somewhat outwardly spreading and sturdy plant habit.
2. Moderately vigorous growth habit.
3. Dense and bushy growth habit.
4. Dark green-colored leaves.
5. Freely flowering habit.
6. Large decorative type inflorescences with reddish orange and yellow bi-colored ray florets.
7. Good garden performance.

Plants of the new *Dahlia* differ primarily from plants of the female parent selection in inflorescence type as plants of the new *Dahlia* have decorative type inflorescences whereas plants of the female parent selection have semi-cactus type inflorescences. In addition, plants of the new *Dahlia* have shorter internodes than plants of the female parent selection.

Plants of the new *Dahlia* differ primarily from plants of the male parent selection in plant size as plants of the new *Dahlia* are taller than plants of the male parent selection. In addition, plants of the new *Dahlia* have bi-colored ray florets whereas plants of the male parent selection do not have bi-colored ray florets.

Plants of the new *Dahlia* can be compared to plants of *Dahlia hybrida* 'XXL Sunset', not patented. In side-by-side comparisons, plants of the new *Dahlia* differ from plants of 'XXL Sunset' in the following characteristics:

1. Plants of the new *Dahlia* have slightly larger inflorescences than plants of 'XXL Sunset'.
2. Ray floret color of plants of the new *Dahlia* are reddish orange and yellow bi-colored whereas ray florets of plants of 'XXL Sunset' are salmon and yellow bi-colored.

Plants of the new *Dahlia* can also be compared to plants of *Dahlia hybrida* 'BKDAMAGFR', disclosed in U.S. Plant Pat. No. 30,692. In side-by-side comparisons, plants of the new *Dahlia* differ from plants of 'BKDAMAGFR' in the following characteristics:

1. Plants of the new *Dahlia* have decorative type inflorescences whereas plants of 'BKDAMAGFR' have cactus type inflorescences.
2. Inflorescences of plants of the new *Dahlia* are held higher above the foliar plane than inflorescences of plants of 'BKDAMAGFR'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet (FIG. 1) is a side perspective view of a typical flowering plant of 'BKDAMAGFF' grown in a container.

Figure 2:
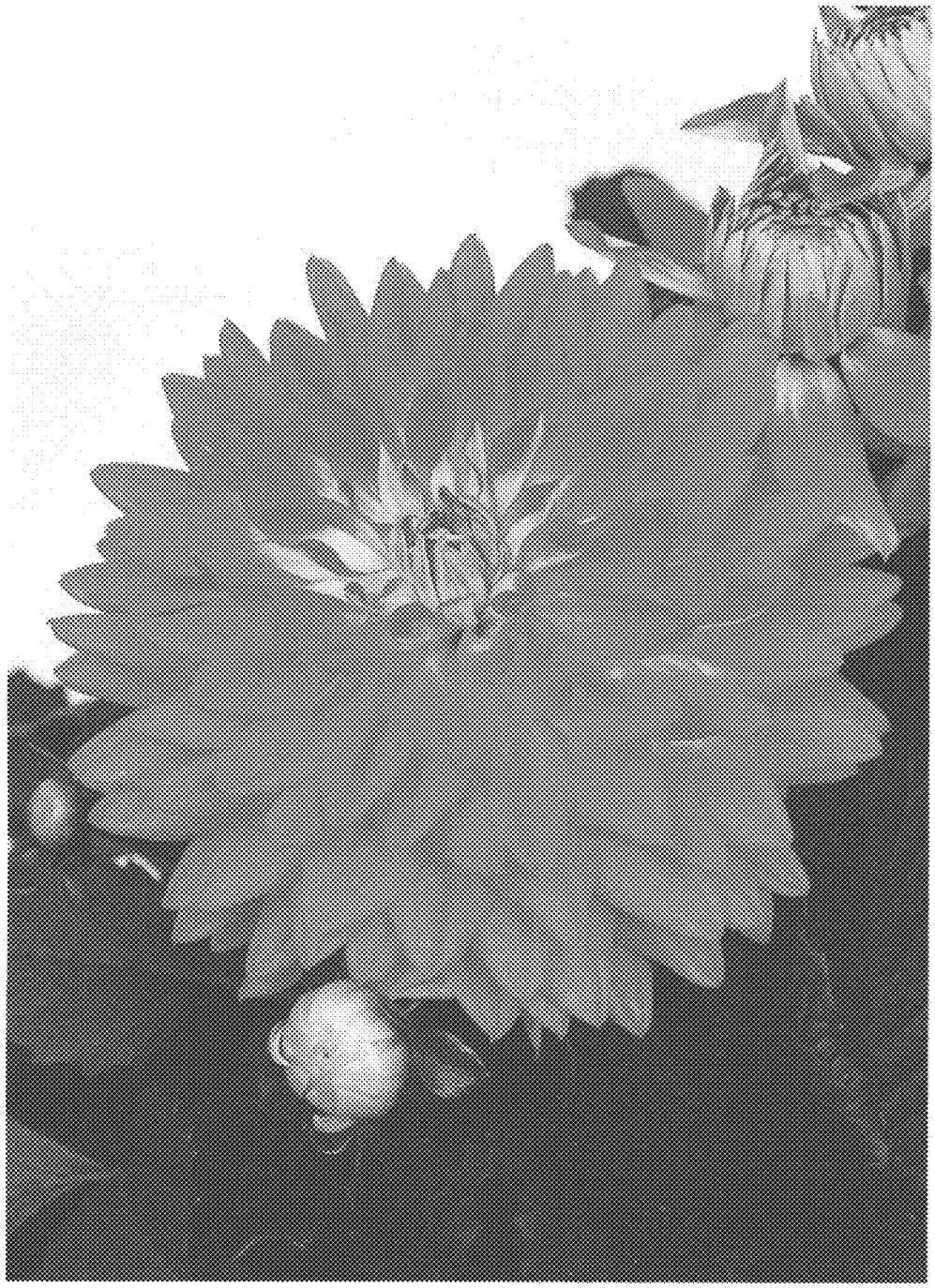

The photograph on the second sheet (FIG. 2) is a close-up view of typical inflorescences of 'BKDAMAGFF'.

DETAILED BOTANICAL DESCRIPTION

The aforementioned photographs and the following observations and measurements describe plants grown during the autumn and winter in 19-cm containers in a glass-covered greenhouse in Maasdijk, The Netherlands and under cultural practices typical of commercial *Dahlia* production. During the production of the plants, day and night temperatures ranged from 17° C. to 19° C. Plants were pinched one time and were eleven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Dahlia hybrida* 'BKDAMAGFF'.

Parentage:

*Female, or seed, parent*.—Proprietary selection of *Dahlia hybrida* identified as code number FET.S15.001.002, not patented.

*Male, or pollen, parent*.—Proprietary selection of *Dahlia hybrida* identified as code number FET.S15.001.032, not patented.

Propagation:

*Type*.—By terminal cuttings.

*Time to initiate roots, summer*.—About 16 days at temperatures ranging from 18° C. to 21° C.

*Time to initiate roots, winter*.—About 19 days at temperatures about 21° C.

*Time to produce a rooted young plant, summer*.—About 21 days at temperatures ranging from 18° C. to 21° C.

*Time to produce a rooted young plant, winter*.—About 23 days at temperatures ranging from 19° C. to 21° C.

*Root description*.—Medium in thickness, fibrous; typically creamy white to light brown in color, actual color of the roots is dependent on substrate composition, water quality, fertilizers, substrate temperature and physiological age of roots; tuber development has not been observed on plants of the new *Dahlia*.

*Rooting habit*.—Moderately freely branching; medium density.

Plant description:

*Plant and growth habit*.—Upright to somewhat outwardly spreading and sturdy plant habit; overall plant shape, roughly globular to flattened globular; freely basal branching habit with about three branches developing per plant; inflorescences held above the foliar plane on strong peduncles; bushy and dense growth habit; pinching is not required but will improve branching habit; moderately vigorous growth habit and moderate growth rate.

*Plant height, soil level to top of foliar plane*.—About 21.7 cm.

*Plant height, soil level to top of floral plane*.—About 29 cm.

*Plant diameter or spread*.—About 39.5 cm.

*Lateral branches*.—Length: About 9.5 cm. Diameter: About 1 cm. Internode length: About 2.3 cm. Aspect: Primary branches are about 20° from vertical; secondary branches are about 35° from primary branch axis. Strength: Moderately strong to strong. Texture and luster: Moderately pubescent; slightly glossy. Color, developing: Close to 144A. Color, developed: Close to 146A to 146B; proximally, tinged with close to N77C; at the internodes, close to 146A to 146B.

Leaf & leaflet description:

*Arrangement*.—Leaves opposite and compound with typically five leaflets and occasionally, three leaflets.

*Length, leaf*.—About 22.3 cm.

*Width, leaf*.—About 22.8 cm.

*Length, terminal leaflets*.—About 11.1 cm.

*Width, terminal leaflets*.—About 7.1 cm.

*Length, lateral leaflets*.—About 10.6 cm.

*Width, lateral leaflets*.—About 6.2 cm.

*Shape, leaves*.—Broadly ovate to close to reniformin outline.

*Shape, leaflets*.—Broadly ovate to broadly elliptic.

*Apex, leaflets*.—Apiculate.

*Base, leaflets*.—Short to long attenuate.

*Margin, leaflets*.—Coarsely serrate to dentate.

*Venation pattern, leaflets*.—Pinnate.

*Texture and luster, upper surface, leaflets*.—Mostly smooth, glabrous with main vein, sparsely pubescent; slightly rugose; slightly glossy.

*Texture and luster, lower surface, leaflets*.—Mostly smooth, glabrous with venation, moderately pubescent; slightly rugose; very slightly glossy.

*Color*.—Developing leaflets, upper surface: Close to 137A. Developing leaflets, lower surface: Close to 147B. Fully expanded leaflets, upper surface: Darker than between NN137A and N189A; venation, close to 146A. Fully expanded leaflets, lower surface: Close to between 189A and 189B; venation, close to 146A to 146B.

*Petioles*.—Length: About 3.7 cm. Diameter: About 6 mm by 7 mm. Strength: Moderately strong to strong. Texture and luster, upper surface: Sparsely pubescent; moderately glossy. Texture and luster, lower surface: Sparsely pubescent; glossy. Color, upper surface: Close to 146B moderately tinged with close to 183B; towards the margins, close to 146A. Color, lower surface: Close to 146B.

Inflorescence description:

*Appearance and arrangement*.—Large decorative type inflorescences with ray and disc florets forming acropetally on a receptacle; inflorescences positioned above and beyond the foliar plane on strong peduncles; inflorescences face mostly upright to slightly outwardly; freely flowering habit with about 15 developing and fully developed inflorescences per plant at one time.

*Fragrance*.—None detected.

*Flowering response and flowering period*.—Early flowering habit, plants begin flowering about 79 days after planting; plants flower continuously during the autumn into the winter in The Netherlands.

*Post-production longevity*.—Inflorescences maintain good substance for about ten days on the plant; inflorescences persistent.

*Inflorescence buds*.—Height: About 3.8 cm. Diameter: About 2.7 cm. Shape: Broadly ovate; involucral bracts moderately reflexed. Texture and luster: Smooth, glabrous; glossy. Color: Close to 144A; proximally, close to 143B; distally, close to 164B; involucral bracts, close to NN137C.

*Inflorescence size*.—Diameter: Large, about 14.1 cm. Depth (height): About 9.8 cm. Disc diameter: About 1.7 cm; typically inconspicuous.

*Receptacles*.—Height: About 7 mm. Diameter: About 1.1 cm. Shape: Lunate. Color: Close to 146B and 146D.

*Ray florets*.—Quantity per inflorescence and arrangement: About 200 arranged in about twelve whorls. Length: About 5.3 cm. Width: About 1.9 cm. Shape: Oblanceolate to narrowly obovate; moderately carinate and moderately convex. Apex: Broad and bluntly acute. Base: Cuneate. Margin: Entire. Aspect: Slightly upright to mostly horizontal; with subsequent development, slightly downward. Texture and luster, upper surface: Smooth, glabrous; velvety; matte. Texture and luster, lower surface: Smooth, glabrous; moderately velvety; mostly matte with venation, slightly glossy. Color: When opening, upper surface: Close to 42A; distally, slightly tinged with close to N25C; towards the base, close to 24A to 24B. When opening, lower surface: Close to 165C tinged with close to N30A and N30B; towards the base, close to 154B to 154C. Fully opened, upper surface: Distally, close to N30A and towards the apex, tinged with close to 33A; proximally, close to 1A and 1B; venation, similar to lamina colors; with subsequent development, close to 44B and towards the apex, tinged with close to 26A and 26B and towards the base, close to 13B. Fully opened, lower surface: Distally, close to 29B to 29C tinged with close to N34D; proximally, close to 1B; venation, close to 154A to 154B; with subsequent development, close to 31C and 31D tinged with close to 33A and 33B and towards the base, close to 2B.

*Disc florets*.—Quantity per inflorescence and arrangement: About 60 massed at the center of the inflorescence in about four spiral whorls. Length: About 1.4 cm. Diameter: About 5 mm. Shape: Tubular, elongated; lower 90% fused and upper 10% free; apices, acute and reflexed. Texture and luster, inner and outer surfaces: Smooth, glabrous; glossy. Color, when opening, inner and outer surfaces: Apex: Close to 13B. Mid-section: Close to 17A. Base: Close to 154B. Color, fully opened, inner and outer surfaces: Apex and mid-section: Close to 15A. Base: Close to 1A to 1B.

*Phyllaries*.—Quantity per inflorescence and arrangement: About five to eight arranged in a single whorl. Length: About 2.4 cm. Width: About 1.1 cm. Shape: Oblanceolate; proximally, strongly carinate. Apex: Acute. Base: Cuneate. Margin: Entire. Texture and luster, upper and lower surfaces: Smooth, glabrous; glossy. Color, upper surface: Close to NN137A. Color, lower surface: Close to NN137C; venation, close to 139A.

*Peduncles*.—Length, terminal peduncle: About 12.8 cm. Diameter, terminal peduncle: About 5 mm. Strength: Strong. Aspect: Mostly upright. Texture and luster: Sparsely to moderately pubescent; slightly glossy. Color: Close to 148A to darker than 148A; proximally, close to 144A.

*Reproductive organs*.—Androecium, present on disc florets only: Quantity per floret: About five. Filament length: About 4 mm. Filament color: Close to 157D. Anther size: About 4 mm by 0.5 mm. Anther shape: Narrowly oblong. Anther color: Close to 13A and 13B. Pollen amount: Abundant. Pollen color: Close to 24A. Gynoecium, present on disc florets only: Quantity per floret: One. Pistil length: About 9 mm. Style length: About 5 mm. Style color: Close to 154C to 154D. Stigma diameter: About 5 mm. Stigma shape: Cleft. Stigma color: Close to 17A. Ovary color: Close to 145D. Seeds and fruits: To date, seed and fruit development have not been observed on plants of the new *Dahlia*.

Pathogen & pest resistance: To date, plants of the new *Dahlia* have not been observed to be resistant to pathogens and pests common to *Dahlia* plants.

Garden performance: Plants of the new *Dahlia* have been observed to have good garden performance, to tolerate high temperatures of about 35° C. and to be suitable for USDA Hardiness Zones 9 to 11.

It is claimed:

1. A new and distinct *Dahlia* plant named 'BKDAM-AGFF' as illustrated and described.

* * * * *